United States Patent
Grüner et al.

(10) Patent No.: US 12,402,869 B2
(45) Date of Patent: *Sep. 2, 2025

(54) INPUT UNIT FOR A MEDICAL INSTRUMENT AND MEDICAL SYSTEM WITH AN INPUT UNIT

(71) Applicant: KARL STORZ SE & Co. KG, Tuttlingen (DE)

(72) Inventors: Sven Axel Grüner, Tuttlingen (DE); Janosz Schneider, Tuttlingen (DE); Dominik Längle, Tuttlingen (DE); Jochen Stefan, Tuttlingen (DE); Thorsten Ahrens, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 574 days.

This patent is subject to a terminal disclaimer.

(21) Appl. No.: 17/869,869

(22) Filed: Jul. 21, 2022

(65) Prior Publication Data

US 2023/0030465 A1 Feb. 2, 2023

(30) Foreign Application Priority Data

Jul. 28, 2021 (DE) ...................... 10 2021 119 613.2

(51) Int. Cl.
*A61B 17/00* (2006.01)
*A61B 34/00* (2016.01)
*A61B 34/30* (2016.01)

(52) U.S. Cl.
CPC ........ *A61B 17/00234* (2013.01); *A61B 34/30* (2016.02); *A61B 34/74* (2016.02); *A61B 2034/301* (2016.02)

(58) Field of Classification Search
CPC ..... A61B 17/2909; A61B 34/30; A61B 34/70; A61B 34/71; A61B 34/74; A61B 17/00234; G06F 3/0338; G06F 3/0362
(Continued)

(56) References Cited

U.S. PATENT DOCUMENTS 5,454,827 A 10/1995 Aust et al.
7,113,836 B2 9/2006 Hörnig
(Continued)

FOREIGN PATENT DOCUMENTS

DE 102004010205 B3 10/2005
DE 102017103199 A1 8/2018
(Continued)

OTHER PUBLICATIONS

Office Action for corresponding German Patent Application No. 10 2021 119 613.2, mailed Mar. 23, 2022.
(Continued)

*Primary Examiner* — Crystal J Barnes-Bullock
(74) *Attorney, Agent, or Firm* — Jason H. Vick; Amped IP LLC

(57) ABSTRACT

One exemplary embodiment relates to an input unit (10) for operating a medical instrument (12) with a hollow shaft (14) extending along a longitudinal axis (L) for receiving guide wires (20), with a tool (16) arranged on the distal side of the shaft (14), extending along an extension axis (E) and a control unit (18) arranged proximally on the shaft (14) for handling the tool (16) by means of the guide wires (20), comprising first input means (22) for continuous, pivoting
(Continued)

and rotation-true, preferably uninterrupted and/or absolute, conversion of an ergonomically limited user input, in particular a natural user movement of movable first operating means, into an adjustment movement of the tool (16) in a first handling mode, in order to pivot the tool (16) by means of the control unit (18) relative to the longitudinal axis (L) in a limited way and/or to rotate about the extension axis (E) in a limited way.

19 Claims, 5 Drawing Sheets

(58) Field of Classification Search
USPC .......................... 700/83, 264; 715/701, 702
See application file for complete search history.

(56) References Cited

U.S. PATENT DOCUMENTS

| | | | |
|---|---|---|---|
| 12,185,927 B2 * | 1/2025 | Schneider | ............. A61B 34/70 |
| 2005/0195946 A1 | 9/2005 | Hornig | |
| 2018/0228560 A1 | 8/2018 | Ziegenspeck et al. | |
| 2021/0038331 A1 | 2/2021 | Grüner | |
| 2021/0379332 A1 | 12/2021 | Komp et al. | |

FOREIGN PATENT DOCUMENTS

| | | | | |
|---|---|---|---|---|
| DE | 102017123163 A1 | | 4/2019 | |
| DE | 102019121092 A1 | | 2/2021 | |
| DE | 102021119618 B4 | * | 2/2023 | ............. A61B 34/70 |
| DE | 102021119646 B4 | * | 7/2023 | ............. A61B 34/30 |
| EP | 3919021 A1 | | 12/2021 | |
| WO | WO 2020/222076 A1 | | 11/2020 | |
| WO | WO-2023006682 A1 | * | 2/2023 | ............. A61B 34/70 |

OTHER PUBLICATIONS

German Office Action for corresponding German Patent Application No. 10 2021 119 641.8, mailed May 3, 2022.

Office Action for U.S. Appl. No. 17/869,878, mailed Sep. 23, 2024.

Notice of Allowance for U.S. Appl. No. 17/869,878, mailed Oct. 29, 2024.

* cited by examiner

INPUT UNIT FOR A MEDICAL INSTRUMENT AND MEDICAL SYSTEM WITH AN INPUT UNIT

CROSS-REFERENCE TO RELATED APPLICATIONS

This application claims the benefit under 35 U.S.C. 119(a) to German Patent Application No. 10 2021 119 613.2, filed 28 Jul. 2021, the disclosure of which is incorporated herein by reference in its entirety.

BACKGROUND

One exemplary aspect relates to an input unit for operating a medical instrument according to the preamble of claim 1. Furthermore, one aspect relates to a medical system with at least one input unit and at least one medical instrument.

A generic input unit for operating a medical instrument is known from U.S. Pat. No. 5,454,827 A, for example.

The known medical instrument comprises a hollow shaft extending along a longitudinal axis for receiving guide wires, the shaft having a tool formed along an extension axis on the distal side and a control unit on the proximal side, which is formed for handling the tool using the guide wires. The control unit has a spatially adjustable disc which is coupled to four guide wires and can pivot the tool relative to the longitudinal axis via pivoting members arranged on the distal side.

To control the handling of the medical instrument, a generic input unit with first input means is provided, which can be operated by an operator's hand. Ergonomic user inputs from the operator are thus converted continuously, that is to say pivoting and/or rotation-true, to the handling of the tool. In addition to simply pivoting the tool to influence the orientation, the tool can also be additionally handled via operating means, for example to adjust a tool designed as a jaw part between an open and closed state. Furthermore, a limited rotation of the tool can be implemented by rotating the gripped input unit, wherein the rotation is represented by the natural freedom of movement of the operator's hand and/or arm.

When controlling the medical instrument, the adjustment movements of the tool always follow the natural movements of the operator's hand or arm, specifically in an uninterrupted and/or absolute manner. In other words, the mechanically coupled tool continuously follows the operator's ergonomically limited user inputs so that the operator is always in control of the tool and precise work is thus made possible during operational use.

As a result, the generic input units enable minimally invasive medical operations to be carried out precisely, for example in order to take tissue samples, sew up tissue or carry out other operational actions in a sensitive environment.

A disadvantage of the known input unit is the limited and/or restricted handling of the tool, since the natural user movement is reproduced pivoting and/or rotation-true, which is why, in addition to the mechanical and/or structural limitation of the tool, there is a limitation due to the degree of natural freedom of the operator's movement.

Furthermore, medical instruments are also known, which, by means of a spindle, enable the tool to rotate in a mechanically limited manner in some areas for a limited range of rotation. Input units are used for the control, which enable the tool to be controlled in a rotation-true manner, wherein the operator breaks the restricted freedom of movement in the control system to overcome the operator's restricted freedom of movement, such that the operator grasps the first input means, or there is a brief interruption and/or decoupling between the input unit and the tool for resetting and/or returning the first input means, which is always associated with a momentary loss of control over the tool.

Moreover, now a promising further development of the medical instrument is described, which is described in document DE 10 2019 121 092 A1 of the applicant. To put it simply, improved mechanics now make it possible for the tool to rotate endlessly about its extension axis. Advantageously, the rotation of the tool can also be carried out independently of the pivoting of the tool, which is why the field of application of the medical instrument is significantly expanded. The control of a medical instrument that has been further developed in this way is now problematic, since the control of an endless rotation can no longer be reproduced in a pivoting and/or rotation-true manner of the user movement. Since in operational use two tools are usually controlled using each hand of the operator, control using two-hand operation is ruled out. Furthermore, the operator should always retain control of the tool, so that there is always an uninterrupted coupling between the first input means and the tool, regardless of the control of the endless rotational movement of the tool, in order to ensure that the user movements are reproduced in a pivoting and/or rotation-true, preferably pivoting and/or rotation-true similar manner, on the tool.

One exemplary aspect is therefore based on the object of proposing an input unit which overcomes the disadvantages known from the prior art. In particular, one aspect is to specify an input unit which, despite the continuous, pivoting and/or rotation-true conversion of an ergonomically limited user input, makes it possible to control an endless rotation of the tool.

Furthermore, the object consists of specifying a medical system with at least one input unit and at least one medical instrument.

This aspect can be achieved by an input unit having the features of claim 1. Furthermore, the exemplary aspect is achieved by a medical system.

Advantageous developments are specified in the dependent claims. All combinations of at least two features disclosed in the description, the claims and/or the figures fall within the scope of the present disclosure.

An input unit with first input means and second input means is provided within the scope of the present disclosure. The input unit according to one aspect of the present disclosure is designed for operating a medical instrument with a hollow shaft extending along a longitudinal axis for receiving guide wires, with a tool being arranged at a first or distal end of the shaft, which extends along an extension axis. Furthermore, a control unit for handling the tool by means of the guide wires is provided at a second or proximal end of the shaft. The first input means are designed for the continuous, pivoting and/or rotation-true conversion of an ergonomically limited user input from an operator into an adjustment movement of the tool in a first handling mode, in order to pivot the tool relative to the longitudinal axis using the first input means using the guide wires via the control unit and/or to rotate about the extension axis. Due to the structural design of the shaft, which is designed to be rigid in some areas, a pivoting of the tool in relation to the longitudinal extent of the shaft is only possible over a limited pivoting range. Furthermore, the rotation of the tool is only possible over a limited range of rotation, which is due to the natural mobility of the operator, in particular a hand of the operator gripping the first operating means, which then in relation to the continuous, i.e., absolute, introduction of a rotation due to the structure of the human arms and whose ergonomics are limited in terms of the range of rotation.

According to one aspect, operating means for handling the tool are provided as the first input means, which continuously, i.e., without an interruption in the coupling between the operating means and the tool, map a translation, embodiment and/or transformation of the ergonomically limited user input into the handling of the tool.

Furthermore, the input unit comprises second input means, which are designed for at least partially and non-absolutely converting, reshaping and/or translating at least one further user input from the operator in order to control an endless rotational movement of the tool about its extension axis in a second handling mode.

Advantageously, the first input means enable the reproduction of an ergonomic user input by the operator into a precise and continuous control and/or handling of the tool, whereby, despite the precise and continuous control of the tool by means of the first input means, the endless rotation of the tool can also be controlled by the second input means through the further user input.

For the technical embodiment of the first input means, the scope of the present disclosure provides that they are designed as a control handle that can be pivoted relative to a rest position, in particular a joystick, with a first rotary element arranged on the control handle for rotation-true rotation of the tool in the first handling mode. The control handle can thus be gripped by one of the operator's hands. A change in the position of the control handle in relation to a basic position can advantageously be detected and converted into a corresponding positioning of the tool. Furthermore, the first rotary element also enables rotational movements to be detected, which are then mapped into a rotation of the tool. In this context, it is again pointed out that the rotation of the tool cannot be limited to a specific range of rotation, or not only by the first rotary element, but it is additionally limited by the freedom of movement of the operator's hand and/or arm, since there should be no change of grip or a brief interruption of the control by means of the first input means.

In this context, it is pointed out that the tool is preferably used as a jaw part, in particular a jaw clamp, forceps, intestinal forceps, scissors, a needle holder, a probe hook or the like, formed as a surgical tool.

In other words, the input unit enables the first input means to map an ergonomic user input of an operator into the handling of the tool in the first handling mode, which is pivoting and/or rotation-true. The operator thus advantageously retains full control over the tool at all times via the first operating means. In addition, the input unit includes the second input means, which enable the endless rotation of the tool to be controlled in the second handling mode and can preferably be operated independently of the first input means.

According to the one aspect, the first input means are formed by the control handle and the first rotary element, wherein the operator is able to grip the control handle and preferably and simultaneously the first rotary element with one hand. By moving the control handle or rotating the first rotary member about an initial position, the position and orientation of the tool can be changed through ergonomic user input. The ergonomic user movement can be mapped to the tool via the control unit and the guide wires in a pivoting and/or rotation-true way.

Within the scope of the present disclosure, the second input means are designed either as at least one second rotary element for controlling the second handling mode or as switching means for switching the first rotary element between controlling the first and second handling mode.

The input unit thus has either the first rotary element and the at least one second rotary element or the first rotary element in combination with the switching means as the first and second input means. By switching to the second handling mode, the first rotary element can also be preferably operated as the second input means. Accordingly, the endless rotation of the tool can be controlled with the at least one second rotary element or the first rotary element in the second handling mode. This results in a non-absolute embodiment of the further user input.

In a further development, the scope of the present disclosure provides that the switching means are designed as a pressure switch and are arranged on the control handle, in particular on a front face of the control handle, in such a way that the first rotary element and the pressure switch can be operated with one hand and preferably simultaneously. Thus, an operator can pivot the control handle, preferably with one hand, simultaneously rotate the first rotary element with the palm of his or her hand and preferably operate the pressure switch with a thumb in order to switch between the first and second handling modes. The first handling mode can preferably be activated when the pressure switch is released or not actuated, and the second handling mode can be activated when the pressure switch is pressed. The arrangement of the pressure switch advantageously enables uninterrupted monitoring of the tool, in particular also when it is pivoted out of the rest position. An operator therefore does not have to reach around or use a second hand to actuate the switching means.

In addition, it is preferably provided that the first and/or the at least one second rotary element can be rotated about a common extension axis of the pivotable control handle, wherein the first and the at least one second rotary element are arranged in combination one above the other along the extension axis of the control handle such that both rotary elements can be operated with one hand. As a result, a rotation in the first handling mode can be carried out with the first rotary element and, independently of this, an endless rotation can be carried out by means of the at least one second rotary element, for example to adjust the tool relative to an orientation of the first rotary element and thus to expand the ergonomically operable rotary movement of the tool.

As an alternative or in addition to the pressure switch mentioned, the first rotary element itself can be translated as a switching means between a first position and at least a second position along the extension axis of the control handle, in order to switch between the first and the second handling mode in addition to the input of the rotational movement, wherein the first rotary element can preferably be locked in the first or at least one second position. Advantageously, the operation of the control handle and switching between the first and the second handling mode can be done with one hand and without having to change the grip, so that the tool can be continuously controlled. The second handling mode can preferably be executed in the at least one second position.

In the previously described embodiments, the first rotary element is preferably designed to be freely rotatable.

In a further alternative or additional embodiment, the first rotary element is freely mounted in sections and can rotate against an end stop as switching means. As a result, further user input in the second handling mode and control of the endless rotation of the tool can preferably be activated by rotating the first rotary element into the end stop.

The end stop is particularly and preferably designed as a spring mechanism in such a way that the switching means can be switched over when a force and/or torque is applied to the spring mechanism, in particular the first rotary element, when a threshold value is reached and/or exceeded. The spring mechanism specifies a kind of pressure point for the operation of the first rotary element, so that an operator only triggers the second handling mode and thus endless rotation after overcoming the torque threshold value. Alternatively or additionally, the control handle can also be connected to such a spring mechanism, so that when a force threshold value is reached and/or exceeded on the control handle in an actuation direction, in particular by a translational application of force along the extension axis of the control handle, the switching means can be switched over.

In a further preferred embodiment, the at least one second rotary element is rotatably mounted about a rest position, in particular by means of a restoring torsion spring, in order to control a speed and a direction of the endless rotary movement of the tool in the second handling mode by means of the further user input. The speed of the endless rotation can be adjustable through the degree of deflection or an input angle.

In a further development, it is provided that the input unit storage means with different stored transfer functions for converting the rotational movement of the ergonomic or other user input into the rotational movement of the tool can be selected using the second input means, wherein the second input means are designed either as various second rotary elements with differently assigned transfer functions or as switching means to select the transfer function of the first rotary element. A specific transfer function can therefore be called up and selected on the storage means with the switching means. In addition to switching between the first and second handling modes, the switching means are preferably also designed to select a transfer function. Thus, the different transfer functions can be selected preferably by means of a key combination or by pressing the switching means, in particular a pressure switch, for a specific period of time. For example, it is possible to switch to another stored or predetermined transfer function by briefly operating the pressure switch. Alternatively, an adjustable first rotary element can also be designed as a switching means to switch between the transfer functions, in particular switching means that can be moved into different locking positions along the extension axis of the control handle.

In this context, it is preferably provided that the input unit is designed with storage means in such a way that the transfer function of the ergonomic user input in the first handling mode is in the form of an input angle, in particular in a first or second limited angular range, from a rest position to a larger or smaller one, in particular rotation-like and/or increasing or decreasing the output angle of the rotational movement of the tool as a function of time, wherein several different transfer functions are able to be combined in sections. However, it is preferably provided that when the ergonomic user input is returned to the rest position, the tool can likewise be rotated into the original rest position. For fine and very precise rotations of the tool, in particular if the tool is shown optically enlarged by display means during a medical operation, a transfer function with a reducing output angle can preferably be selected. Otherwise, for fast and large turns, a limited gain transfer function with a larger output angle is preferably selectable. For example, a time-dependent or dynamically increasing transfer function can be used to simply switch from said fine output angle to a larger output angle during user input, or vice versa.

In this context, it is also provided that the input unit is designed with storage means in such a way that the transfer function converts the further user input in the second handling mode in the form of an input angle, preferably a third angular range that increases to the first and second angular ranges, into a fast or slow and/or dynamically increasing or decreasing the output speed of the endless rotation of the tool. As a result, a transfer function can preferably also be selected in the second handling mode by means of various second rotary elements with different transfer functions or by actuating the switching means. In particular, by moving the first rotary element into various second positions along the control handle, the further user input in the second handling mode can also be transferred to the endless rotational movement of the tool with different transfer functions.

In a preferred embodiment, the transfer function on the storage means can be selected, in particular automatically, as a function of the tool connected to the medical instrument. Different transfer functions with different output angles or output angular velocities can be predetermined in particular for tools such as a needle holder, intestinal forceps or a probe hook. The transfer function is therefore advantageously preconfigured on the storage means depending on the selected tool, so that the correct transfer function can be automatically set when using the respective tool.

Furthermore, it is conceivable to set the transfer function as a function of the magnification optics used, wherein the output angle and the output angular velocity preferably is converted to be smaller or reduced as the magnification of the tool image increases.

Furthermore, the assignment of which rotary wheel can be operated in which handling mode and with which transfer function is preferably selectable by an operator. In this case, the functionality of the switching means with regard to the change between the two handling modes and the transfer functions can preferably also be selected, in particular by the operator.

In a further embodiment, the first rotary element and preferably the tool has markings in order to clarify in the first handling mode an absolute or rotation-true conversion of the ergonomic user input into the rotary movement of the tool with a corresponding marking, in particular to visually check the match of an input angle of the first rotary element with the output angle of the tool. Due to the endless rotation of the tool, the tool and the input means can be adjusted relative to one another. By means of the markings, the tool can be returned to a starting position in relation to the input means in a simple, manual or automatic manner, in particular by means of the endless rotational movement.

In addition, within the scope of the present disclosure, protection is claimed for a medical system, in particular an end effector and/or a surgical robot, which has at least one input unit and at least one medical instrument.

The at least one medical instrument includes a hollow shaft extending along a longitudinal axis, a control unit, and a tool for surgical use.

The shaft is designed to receive guide wires for mechanically steering the tool, the tool being arranged at a distal end of the shaft and extending along an extension axis.

The control unit is arranged on the proximal end of the shaft and is operatively connected to the tool via the guide wires in order to pivot the tool in a first handling mode, in particular to pivot it to a limited extent and to rotate it to a limited extent, wherein the tool also can be rotated endlessly via the control unit in a second handling mode.

A preferred medical instrument is described in document DE 10 2019 121 092 A1 of the applicant, wherein full reference is made to the corresponding disclosure and the disclosed features of the medical instrument are hereby incorporated herein by reference in their entirety in the application as part of the disclosure as part of a further development.

The medical instrument preferably has a spatially adjustable disc in order to pivot the guide wires along the longitudinal axis of the shaft, the disc being rotatable about the longitudinal axis together with the shaft and the guide wires, and the control unit preferably being designed to pivot the disc.

The tool is preferably in the form of a jaw part, in particular a jaw clamp, forceps, intestinal forceps, scissors, a needle holder, a probe hook or the like, formed as surgical tool.

BRIEF DESCRIPTION OF THE DRAWINGS

Further advantages and details of the invention result from the following description of preferred embodiments of the invention as well as from purely schematic drawings.

Showing.

DETAILED DESCRIPTION

Identical elements or elements with the same function are provided with the same reference numbers in the figures.

Figure 1:
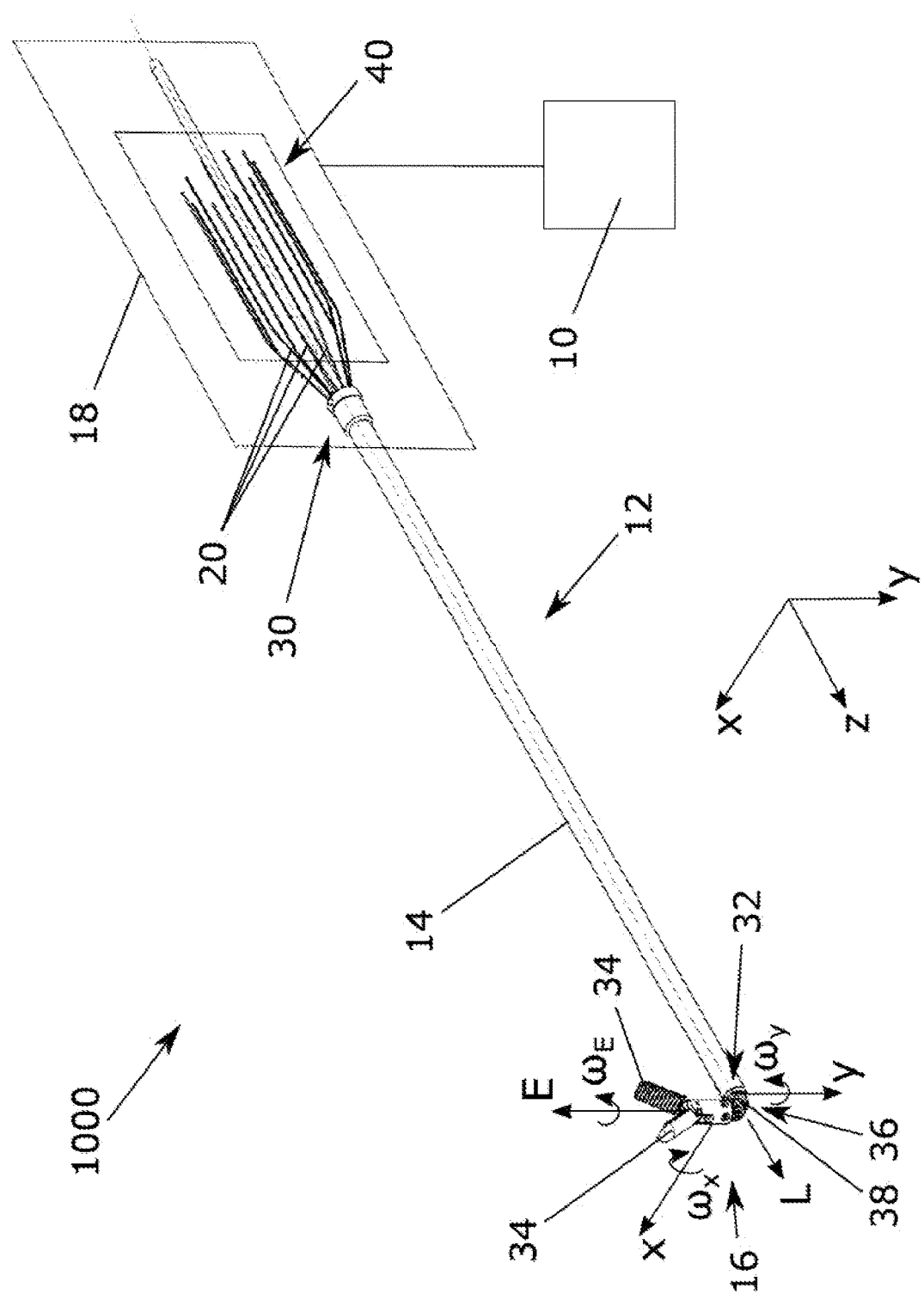
FIG. 1: a perspective view of a medical instrument with an input unit according to an exemplary embodiment shown purely symbolically, in FIG. 2a to FIG. 2c: a perspective view of a tool of the medical instrument according to FIG. 1 and schematised first input means of the input unit according to an exemplary embodiment, in FIG. 3a to FIG. 3c: a perspective view of the known tool from FIG. 2 and schematised second input means of the input unit according to an exemplary embodiment, in FIG. 4a: a perspective view of an input unit with a pivotable control handle and a first rotary element, in FIG. 4b: an input unit according to FIG. 4a with a second rotary element, in FIG. 5a to FIG. 5c: an input unit according to FIG. 4a with a translationally adjustable first rotary element.

In FIG. 1 a medical system 1000 with a medical instrument 12 is illustrated, which can be operated using a control unit 10 according to one embodiment designed as a black box. The medical instrument 12 has a hollow shaft 14, which on the proximal side or at a proximal end 30 includes a control unit 18, also illustrated only as a black box, and on the distal side or at a distal end 32, a tool 16, the tool 16 being connected to the control unit 18 in operative connection via guide wires 20.

The control unit 18 enables an endless rotary drive of the tool 16 illustrated in the figure, which is pivoted by 90°. A control unit 18 can be used for this purpose, for example, as is known from the aforementioned document DE 10 2019 121 092 A1 of the applicant.

The tool 16 is a tool 16 provided with jaw elements 34, in particular a jaw part 17, the jaw elements 34 also being adjustable between an open state and a closed state via the control unit 18 like a forceps.

The tool 16 can be pivoted via a joint mechanism 36 relative to the longitudinal axis L of the shaft 14, wherein the joint mechanism 36 is formed by pivoting members 38 arranged at the distal end 32 of the shaft 14, which are connected via guide wires 20 running in the longitudinal direction L of the shaft 14 with an unillustrated drive 40 in the figure and arranged at the proximal end 30 of the shaft 14, such that a movement of the drive 40 on the proximal side and a corresponding relative movement of the pivoting members 38 on the distal side causes the tool 16 to pivot.

A corresponding drive 40 is known, for example, from the aforementioned document DE 10 2019 121 092 A1 of the applicant. The guide wires 20 are connected on the proximal side to a disc, not illustrated in the figure, which can be spatially pivoted and rotated by means of the drives 40. The pivoting of the disc causes the guide wires 20 to partially stretch along the longitudinal axis L of the shaft 14 and the tool 16, which extends in a z-direction of a Cartesian coordinate system, can pivot proportionately about the spatial axes x, y of the Cartesian coordinate system by means of the joint mechanism 36. The pivoting movements $\omega_x$, $\omega_y$ around the spatial axes x, y thus enable a spatial orientation of the tool 16.

Due to the rotation of the shaft 14 together with the guide wires 20 about the longitudinal axis L, the tool 16 can also be rotated permanently or endlessly relative to the control unit 18. By using the pivotable and rotatably mounted disc, the tool 16 can also be adjusted along the longitudinal axis L by the guide wires 20 at the same time for permanent rotation about the longitudinal axis L. As a result, the spatial orientation of the tool 16 can be compensated for permanent rotation of the shaft 14, the tool 16 rotating about its extension axis E with a rotational movement $\omega_E$. If the tool 16 is in a non-pivoted state, the extension axis E of the tool 16 corresponds to the longitudinal axis L of the shaft 14 and extends in the z-direction of the Cartesian coordinate system.

Since the guide wires 20 can rotate about the longitudinal axis L together with the shaft 14, an endless rotation about the longitudinal axis L or the extension axis E can be carried out by means of the drive 40 without twisting the guide wires 20 one into another to form a cord and without limiting or preventing control of the pivoting movement $\omega_x$, $\omega_y$.

Figure 2A:
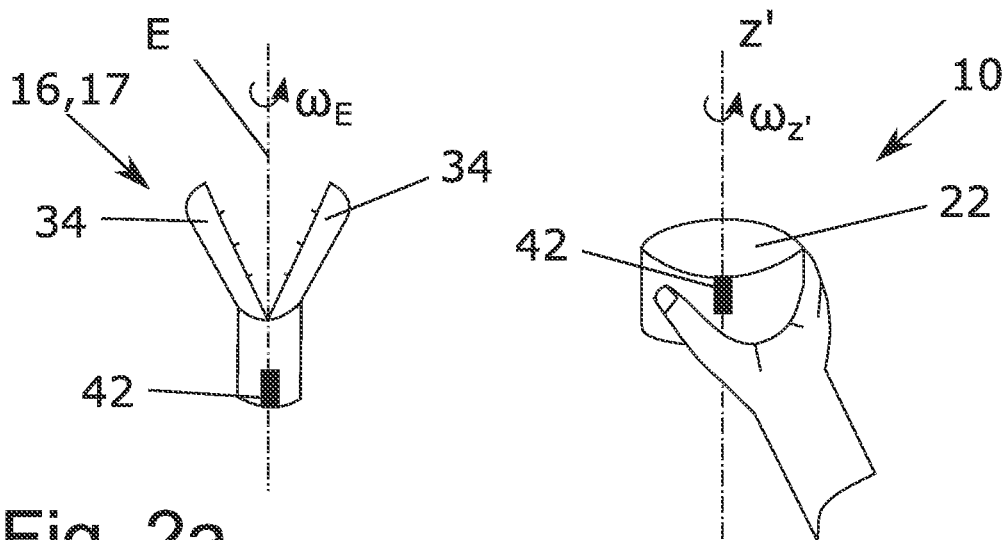
Figure 2B:
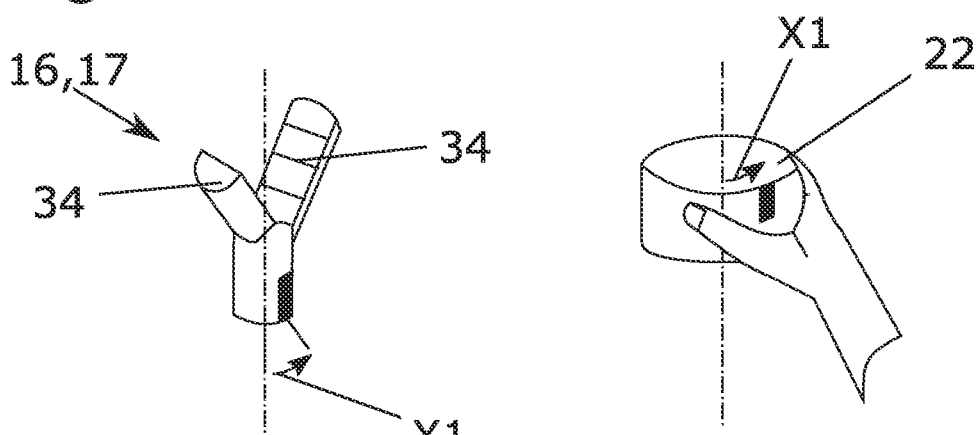
Figure 2C:
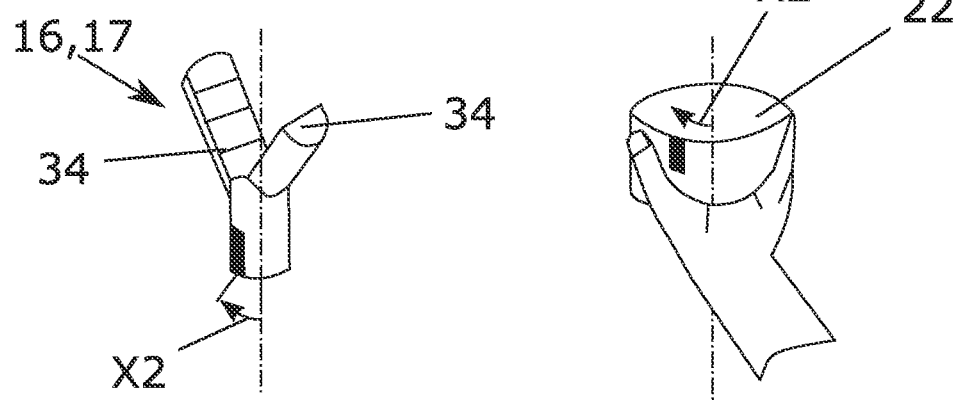

In FIGS. 2a to 2c, to illustrate the functioning of the first input means 22 of the input unit 10 according to one exemplary embodiment, the active principle when converting an ergonomic user input by an operator into handling of the tool 16 designed as a jaw part 17 is shown schematically.

In FIG. 2a, the input unit 10 and the jaw part 17 are shown in a rest position or a basic position, each with markings 42 to clarify the orientation.

In the present case, the first input means 22 are designed as a tangible cylinder which is in operative contact with the unillustrated control unit 18 by means of an unillustrated cardan suspension.

For the sake of simplification, it is assumed that the ergonomic user input is only limited to a rotation of the jaw part 17 about its extension axis E in the first handling mode.

The rotational movement $\omega_z$ of the first input means 22 and the rotational movement $\omega_E$ of the tool 16 are designed to be rotationally accurate to one another in the first handling mode, that is to say they have the same angular speeds in terms of amount.

In FIG. 2b, the first input means 22 were rotated anti-clockwise by a first angular range X1, with this rotational movement being transmitted to the jaw part 17 at the correct angle. Furthermore, the first input means 22 were then rotated clockwise from the position illustrated in FIG. 2b by a second angular range X2 with reference to FIG. 2c, wherein here the jaw part 17 also follows the rotational movement of the first input means 22 in a rotation-true manner.

During ergonomic user input, the operator's hand always remains in contact with the first input means 22, so there should be no gripping around or brief interruptions in the first handling mode, since continuous and preferably uninterrupted imaging of the rotational movement $\omega_z$, in the input means 22 are made in the rotational motion $\omega_E$ of the jaw part 17. An operator therefore has continuous and uninterrupted control over the adjustment movement of the tool 16, in particular in order to be able to carry out precise, complex, minimally invasive interventions and/or medical operations in a sensitive environment.

Due to the physiology of the human hand, the range of rotation is limited to a maximum angle of rotation of approximately ±90° about the resting position and thus a total of approximately 180° about the resting or basic position.

As an alternative to the transfer or embodiment of a first or second angular range (X1, X2) or input angle into a rotation-true output angle illustrated in FIG. 2a to FIG. 2c, the transfer can also take place in a rotation-like manner. The rotational movement $\omega_E$ of the tool 16 continues to follow the rotational movement $\omega_{z'}$ of the first input means 22, in particular a returning ergonomic user input in a basic position according to FIG. 2a. However, the embodiment of the input angle into an output angle can follow different transfer functions, wherein an input angle converts into a larger or smaller and/or time-dependent increasing or decreasing output angle of the rotational movement $\omega_E$ of the tool 16.

The transfer function can preferably be selected, in particular automatically, as a function of the tool 16 connected to the medical instrument 12. A different transfer function can therefore be preconfigured if a cutting or sewing tool is used instead of the jaw part 17 illustrated here.

Figure 3A:
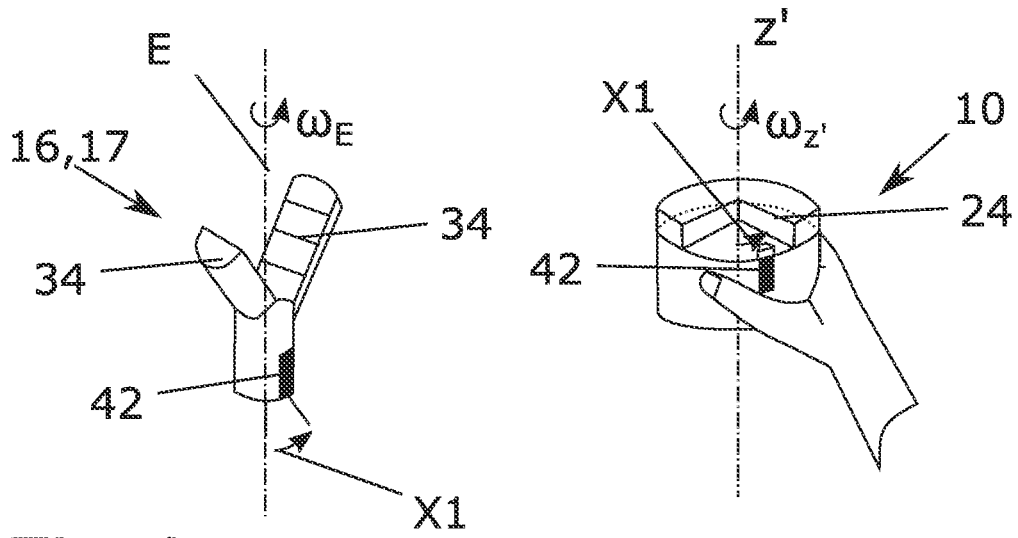
Figure 3B:
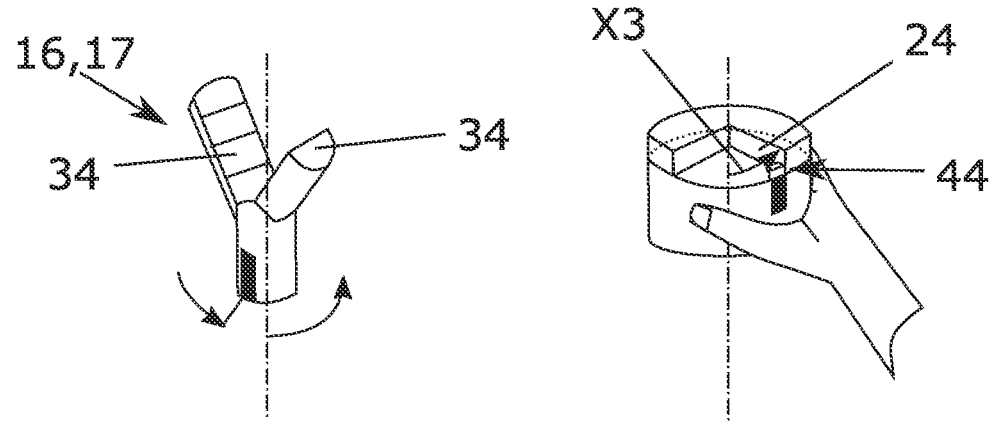
Figure 3C:
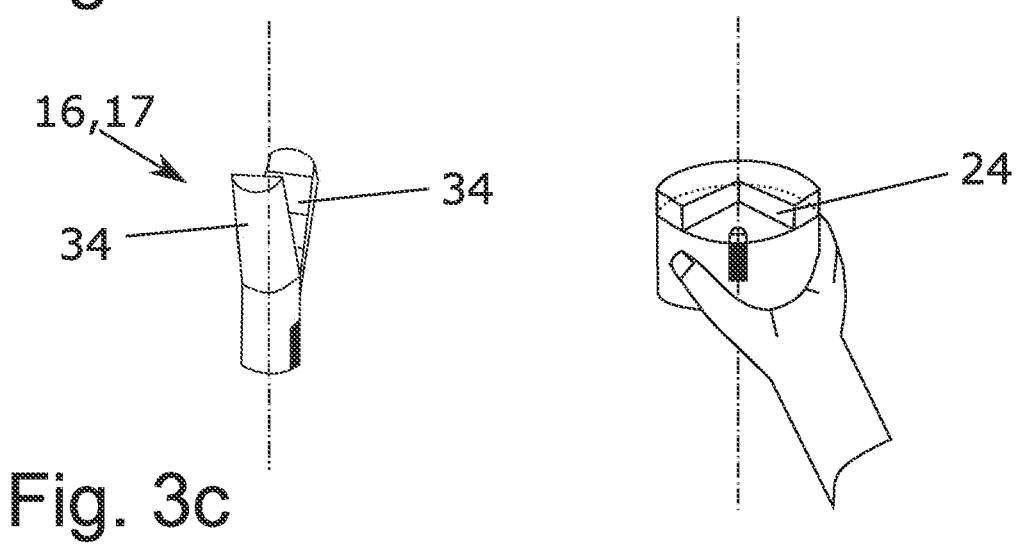

In FIG. 3a to FIG. 3c, in addition to the control of the tool 16 in the first handling mode, the tool 16 is also controlled via the second input means 24 in the second handling mode.

In the present case, the second input means 24 are formed by the identical tangible cylinder in order to control the tool 16 both in the first handling mode and in the second handling mode.

In FIG. 3a, as in FIG. 2b, the first input means 22 and therefore also the second input means 24 have been rotated anticlockwise from the basic position in FIG. 2a about the angular range X1, wherein the angular range X1 was reproduced in a rotation-true manner on the jaw part 17 and caused a corresponding rotation. The tool 18 was thus controlled in the first handling mode.

In FIG. 3b, the cylinder was rotated by a further user movement about the third angular range X3, which is larger than the first angular range X1, as a result of which the second input means 24 were guided to an end stop 44, in which an endless rotational movement of the jaw part 17 is activated. The jaw part 17 thus rotates endlessly about its extension axis E as a result of the further user input 21.

The end stop 44 is preferably designed here as a spring mechanism in such a way that the second handling mode can be executed, in particular the first handling mode can be switched to the second handling mode, by the further user input and reaching and/or exceeding a threshold value of a force and/or torque applied to the spring mechanism.

The input of the third angular range X3 or input angle shown in FIG. 3b preferably also specifies an output angular velocity of the endless rotational movement $\omega_E$. Depending on the transfer function, an input angle in the third angular range X3 can have a fast or slow and/or dynamically increasing or decreasing output angular velocity of the endless rotation $\omega_E$ of the tool 16.

The endless rotation of the tool 16 is interrupted again by returning the second input means 24 to the basic position according to FIG. 3c. For this purpose, the second input means 24 is preferably mounted so as to be resilient about the rest position, in particular by means of a restoring torsion spring not illustrated here. The tool 16 does not, in particular not completely, follow the movement of the second input means 24 back into the basic position, so that the position of the markings 42 of the tool 16 and the input unit 10 can be adjusted relative to one another. It is thus advantageously enabled in the second handling mode by the second input means 24 that, in contrast to the operating principle of the first input means described with reference to FIGS. 2b and 2c, in the first handling mode, the speed of the rotational movement $\omega_E$ is not implemented in a rotation-true manner, at least in sections, in accordance with the further user input. However, further user input is still uninterrupted with the rotational movement $\omega_E$ of the tool 16 in order to ensure full control over the tool movement at all times. Advantageously, the ergonomically operable range of rotation is expanded as desired by the second input means 24 from approximately ±90° about the rest position or basic position, without the operator losing control of the jaw part 17 in the process.

The input unit 10 is illustrated in detail in FIG. 4a to FIG. 5c, wherein the first input means 22 is designed as a control handle 100 that can be pivoted relative to a rest position 102, in particular a joystick, with a first rotary element 104. The control handle 100 is pivotable relative to a base plate 103 or bracket to o with a pivotal movement$_{x'}$, $\omega_{y'}$ about the spatial axes x', y' of the input unit 10, a pivoting movement $\omega_x$, $\omega_y$ of the tool 16 to control. With the first rotary element 104, the operator can preferably enter a rotational movement $\omega_{E'}$ about an extension axis E' of the control handle 100 with one hand to preferably control a rotation-true rotational movement $\omega_E$ of the tool 16.

Figure 4A:
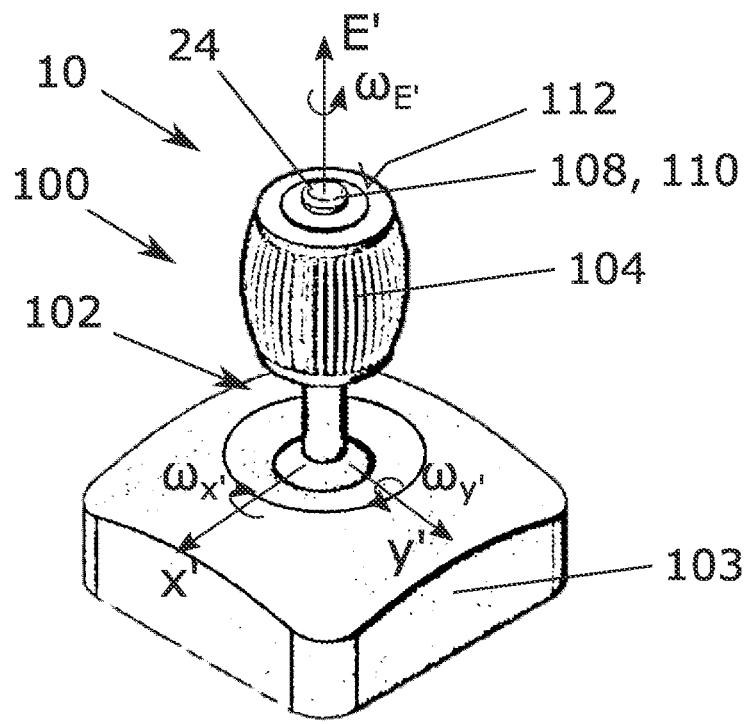

In FIG. 4a, the control handle 100 has, as the second input means 24, the first rotary element 104 in combination with switching means 108, which is designed to switch the first rotary element 104 between controlling the first and second handling mode. The switching means 108 are preferably arranged as a pressure switch 110, in particular a spring-loaded pressure switch 110, and preferably on a front face 112 of the control handle 100. As a result, the first rotary element 104 and the pressure switch 110 can be operated with one hand and preferably simultaneously. By operating the pressure switch 110, preferably with the thumb of an operator, it is possible to switch between controlling the first and second handling mode by means of the first rotary element 104. The arrangement of the pressure switch 110 advantageously enables uninterrupted monitoring of the tool 16, in particular also when it is pivoted out of the rest position 104. The operator therefore does not have to reach around or use a second hand to actuate the switching means 108.

In addition to the selection between the first and second handling mode, the switching means 108 can also be designed to select between different transfer functions, for example by means of a key combination or by pressing the pushbutton switch 110 for a specific period of time. The transfer functions are stored on unillustrated storage means of the input unit and can be called up by switching means 108 or are already assigned to one of rotary elements 104, 106.

Alternatively, it would also be conceivable to arrange the pressure switch 110 in the base plate 103, in which case it can be operated by actuating the control handle 100 along the extension axis E'. Simultaneous one-handed operation of the first rotary element 104 would also be possible in this embodiment.

Figure 4B:
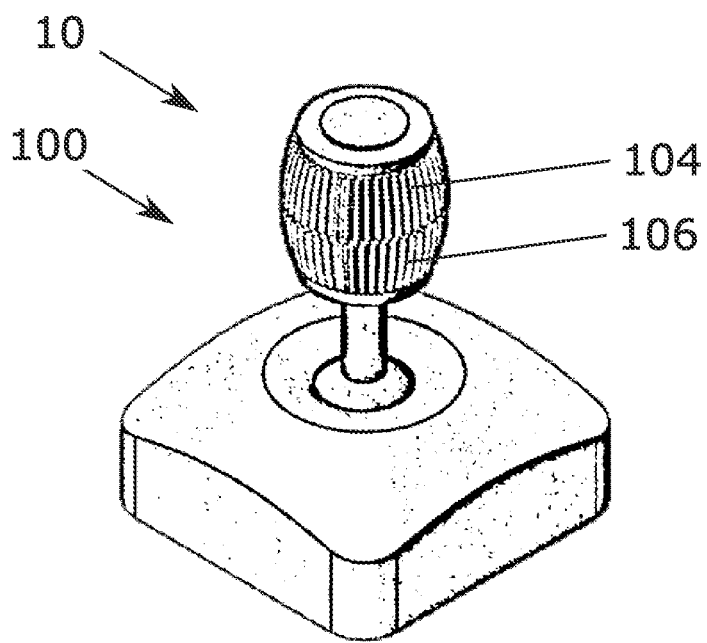

In FIG. 4b, the control handle 100 has the first rotary element 104 as the first input means 22 and a second rotary element 106 as the second input means 24 for controlling the endless rotational movement $\omega_E$ of the tool 16 in the second handling mode. The first and the second rotary element 104, 106 can be rotated about the axis z' of the pivotable control handle 100 and are arranged directly one above the other. Both rotary elements 104, 106 can be rotated independently of one another, wherein both rotary elements 104, 106 are operable with one hand and without a change of grip due to the spatially adjacent arrangement. In addition to the two rotary elements 104, 106 shown, further rotary elements, in particular second rotary elements, with different transfer functions are preferably arranged along the extension axis E' of the control handle 100.

Figure 5A:
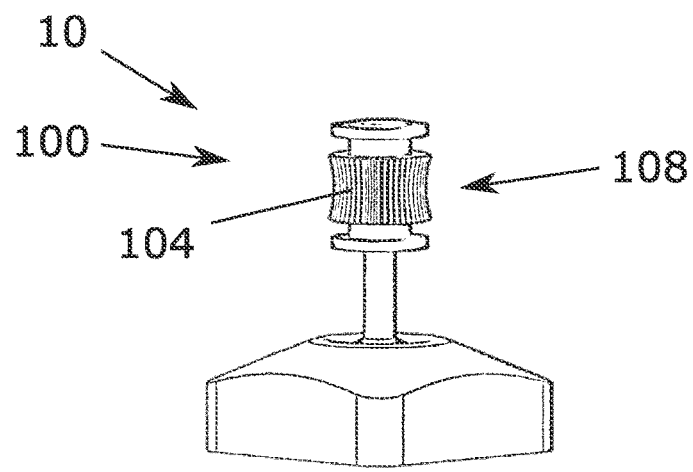

In FIG. 5a the control handle 100 with the first rotary element 104 is illustrated, wherein the first rotary element 104 is a switching means 108 that can be translated along the extension axis z' of the control handle 100.

Figure 5B:
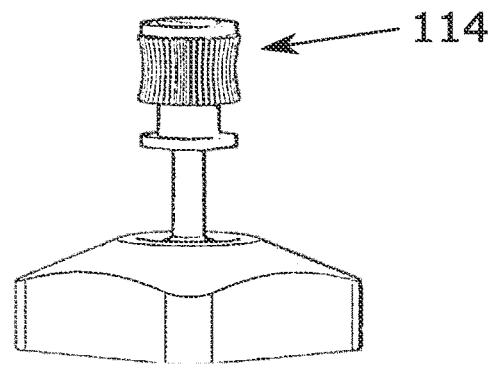
Figure 5C:
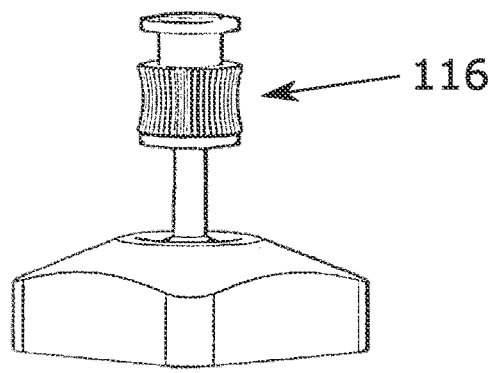

The first rotary element 104 is illustrated in a first position 114 in FIG. 5b and the first rotary element 104 is illustrated in a second position 116 in FIG. 5c.

The first rotary element 104 can thus be adjustable at least between these two positions 114, 116, in order switch between the first and the second handling mode in addition to the rotational movement $\omega_E$. The first rotary element 104 preferably snaps into the first or the second position 114, 116, in order to operate and rotate the first rotary element 104 in the respective first or second handling mode. In addition to switching between the first and second handling mode, it would be conceivable to specify further positions or locking positions, wherein a different transfer function between the input angle and the output angle or the output angular velocity of the tool 16 is selectable depending on the position. For example, the rotary element can also be latched in an intermediate position between the first and second positions 114, 116, in particular various second positions, in order to operate the tool 16 with the first rotary element 114 with different transfer functions.

LIST OF REFERENCE NUMBERS

10 Input unit
12 Medical instrument
14 Shaft
16 Tool
17 Jaw part
18 Control unit
20 Guide wires
22 First input means
24 Second input means
30 Proximal end of the shaft
32 Distal end of the shaft
34 Jaw elements of the tool
36 Joint mechanism
38 Pivoting member
40 Drive
42 Marking
44 End stop
100 Pivoting control handle
102 Rest position
103 Base plate
104 First rotary element
106 Second rotary element
108 Switching means
110 Pressure switch
112 Front face of the control handle
114 First position of the switching means
116 Second position of the switching means
1000 Medical system
E Tool extension axis
L longitudinal axis of the shaft
R Axis of rotation
X1 First angular range
X2 Second angular range
X3 Third angular range
z' Extension axis of the input unit
x, y Spatial axes of the medical instrument
$\omega_E$ Rotational movement of the tool
$\omega_{z'}$ Rotational movement of the input unit
$\omega_x$ Pivoting movement of the tool
$\omega_y$ Pivoting movement of the tool
E' Extension axis of the control handle
x', y' Spatial axes of the input unit
$\omega_{x'}$ Pivoting movement of the control handle
$\omega_{y'}$ Pivoting movement of the control handle

The invention claimed is:

1. An input unit configured for operating a medical instrument having a hollow shaft extending along a longitudinal axis for receiving guide wires, with a tool arranged distally on the shaft and a control unit arranged proximally on the shaft for handling the tool by means of the guide wires, comprising:
    first input means for the continuous, pivoting and/or rotation-true conversion of an ergonomically limited user input into an adjustment movement of the tool in a first handling mode in order to pivot the tool to a limit relative to the longitudinal axis by means of the control unit and/or to rotate it to a limit about the extension axis, wherein
    the input unit has second input means for at least partially, non-absolutely converting at least one further user input into an endless rotational movement ($\omega_E$) of the tool about the tool's extension axis in a second handling mode, wherein the first input means is arranged as a control handle that can be pivoted relative to a rest position with a first rotary element arranged at the control handle for rotation-true rotation of the tool in the first handling mode and the second input means are formed either as at least one second rotary element for controlling the second handling mode or as switching means for switching of the first rotary member between controlling the first and second handling modes.

2. The input unit according to claim 1, wherein the switching means are designed as a pressure switch and are arranged on the control handle in such a way that the first rotary element and the pressure switch can be operated with one hand.

3. The input unit according to claim 1, wherein the first and/or the at least one second rotary element is configured to be rotated about a common extension axis of the pivotable control handle, wherein the first and the at least one second rotary element are arranged one above the other along the extension axis of the control handle, so that the rotary elements can be operated with one hand.

4. The input unit according to one of claim 1, wherein the first rotary element is translationally adjustable as a switching means between a first position and at least a second position along the extension axis of the control handle, in order to switch between the first and the second handling mode in addition to the input of the rotational movement ($\omega_E$), wherein the first rotary element engages in the first or the at least one second position.

5. The input unit according to claim 1, wherein the first rotary element is freely mounted in sections and can rotate against an end stop as switching means.

6. The input unit according to claim 5, wherein the end stop is a spring mechanism configured in such a way that the switching means can be switched over when a force and/or torque is applied to the spring mechanism when a threshold value is reached and/or exceeded.

7. The input unit according to claim 1, wherein the at least one second rotary element is rotatably mounted about a rest position, by a restoring torsion spring, to control a speed and a direction of the endless rotary movement ($\omega_E$) in the second handling mode by the further user input.

8. The input unit according to claim 1, wherein the input unit comprises storage means with different transfer functions for converting the rotational movement ($\omega_z$) of the ergonomic or other user input into the rotational movement ($\omega_E$) of the tool, wherein these transfer functions are selectable by the second input means and wherein the second input means are configured either as various second rotating elements with differently assigned transfer functions, or as switching means configured to select the transfer function of the first rotating element by a key combination or a print time on the switching means.

9. The input unit according to claim 8, wherein the input unit with the storage means is configured such that the transfer function converts the ergonomic user input in the first handling mode in the form of an input angle into a larger or smaller rotation-like, and/or time-dependent increasing or decreasing output angle of the rotational movement ($\omega_E$) of the tool.

10. The input unit according to claim 8, wherein the input unit with the storage means is configured such that a the transfer function converts the further user input in the second handling mode in the form of an input angle into a fast or slow and/or dynamically increasing or decreasing output angular velocity of the endless rotation ($\omega_E$) of the tool.

11. The input unit according to claim 8, wherein the transfer function on the storage means is selected depending on the tool connected to the medical instrument.

12. The input unit according to claim 8, wherein the transfer function on the storage means is automatically selected depending on the tool connected to the medical instrument.

13. The input unit according to claim 1, wherein the first rotating element has markings to identify in the first handling mode an absolute or pivoting and/or rotation-true conversion of an ergonomic user input into a rotational movement ($\omega_E$) of the tool, and for visually checking a match of an input angle of the first rotating element with an output angle of the tool.

14. The input unit according to claim 1, wherein the first input means is a joystick and the first input means provides an uninterrupted and/or absolute conversion of the ergonomically limited user input.

15. The input unit according to claim 1, wherein the first rotary element and the pressure switch can be operated at the same time.

16. The input unit according to claim 1, wherein the ergonomically limited user input is a natural user movement of the movable first operating means.

17. A medical system, according to claim 1, and with at least one medical instrument, comprising a hollow shaft extending along the longitudinal axis for receiving guide wires for a tool, the tool arranged on the distal side of the shaft and formed along an extension axis configured for medical use on patients, a control unit arranged proximally on the shaft and operatively connected to the tool via the guide wires in order to move the tool in a first handling mode and in a second handling mode.

18. The medical system according to claim 17, wherein the medical system comprises a spatially adjustable disc which is in operative contact with the guide wires in order to pivot the tool along the longitudinal axis of the shaft by the guide wires, wherein the disc together with the shaft and the guide wires are endlessly rotatable about the longitudinal axis.

19. The medical system of claim 17, wherein the medical system is an end effector and/or a surgical robot with at least one input unit.

* * * * *